(12) United States Patent
Yotsuya et al.

(10) Patent No.: US 6,664,279 B2
(45) Date of Patent: Dec. 16, 2003

(54) REMEDIES OR PREVENTIVES FOR LIVER DISEASES CONTAINING DIAMINOTRIFLUOROMETHYLPYRIDINE DERIVATIVES

(75) Inventors: Shuichi Yotsuya, Shiga (JP); Kimie Sakai, Shiga (JP)

(73) Assignee: Ishihara Sangyo Kaisha, Ltd., Osaka (JP)

( * ) Notice: Subject to any disclaimer, the term of this patent is extended or adjusted under 35 U.S.C. 154(b) by 0 days.

(21) Appl. No.: 10/182,466

(22) PCT Filed: Jan. 30, 2001

(86) PCT No.: PCT/JP01/00615

§ 371 (c)(1),
(2), (4) Date: Jul. 29, 2002

(87) PCT Pub. No.: WO01/56569

PCT Pub. Date: Sep. 8, 2001

(65) Prior Publication Data

US 2003/0018054 A1 Jan. 23, 2003

(30) Foreign Application Priority Data

Feb. 1, 2000 (JP) .......................................... 2000-24350

(51) Int. Cl.[7] ...................... A61K 31/44; C07D 213/02
(52) U.S. Cl. ...................................... 514/352; 546/308
(58) Field of Search .......................... 546/308; 514/352

(56) References Cited

U.S. PATENT DOCUMENTS

| 5,229,403 A | 7/1993 | Haga et al. ................ 514/352 |
| 5,492,908 A | 2/1996 | Haga et al. ................ 514/222 |
| 6,197,796 B1 | 3/2001 | Ogura ........................ 514/352 |

FOREIGN PATENT DOCUMENTS

| EP | 0 465 913 | * | 1/1992 |
| JP | 5-111383 | | 5/1993 |
| JP | 6-239856 | | 8/1994 |
| JP | 7-69898 | | 3/1995 |
| JP | 10-298076 | | 11/1998 |
| JP | 11-228563 | | 8/1999 |
| WO | WO 98/37887 | * | 9/1998 |

OTHER PUBLICATIONS

A.A. Horton et al.: "Effects of inhibitors of phospholipase A2, cyclooxygenase and thromboxane synthetase on paracetamol hepatotoxicity in the rat" Eicosanoids, vol. 2, No. 2, pp. 123–129 1989.

I.I. Moraru et al.: "Role of phospholipase A2, C and D activities during myocardial ischemia and reperfusion" Ann. N.Y. Acad. Sci., No. 723, pp. 328–332 1994.

I. Saluja et al.: "Activation of cPLA2, PKC, and ERKs in the rat cerebral cortex during ischemia/reperfusion" Neurochem. Res., vol. 24, No. 5, pp. 669–677 1999.

* cited by examiner

*Primary Examiner*—Zinna Northington Davis
(74) *Attorney, Agent, or Firm*—Oblon, Spivak, McClelland, Maier & Neustadt, P.C.

(57) ABSTRACT

A therapeutic or preventive agent for liver diseases, containing as an active ingredient a diaminotrifluoromethylpyridine derivative represented by the formula (I) or its salt:

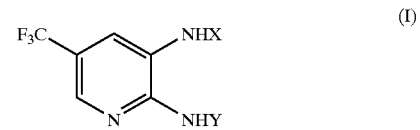

wherein X is a $—CW^1R^1$ group, a $—COCOR^2$ group, a $—CW^1NHCOR^2$ group, a $—C(=W^1)W^2R^3$ group or a $—CW^1N(R^4)R^5$ group; Y is an alkyl group, a $—CW^3R^6$ group, a $—COCOR^7$ group, a $—NHCOR^7$ group, a $—C(=W^3)W^4R^8$ group, a $—(NH)_mSO_2R^9$ group, a $—(NH)_mSO_2OR^{10}$ group or a $—(NH)_mSO_2N(R^{11})R^{12}$ group; each of $R^1$, $R^6$ and $R^9$ is a chain hydrocarbon group, a monocyclic hydrocarbon group, a polycyclic hydrocarbon group, a monocyclic heterocycle group or a polycyclic heterocycle group; each of $R^2$ and $R^7$ is an alkyl group, an alkoxy group, a phenyl group or a phenoxy group; each of $R^3$, $R^8$ and $R^{10}$ is an alkyl group, an alkenyl group, an alkynyl group, a cycloalkyl group, a phenyl group or a benzyl group; each of $R^4$, $R^5$, $R^{11}$ and $R^{12}$ is an alkyl group; each of $W^1$, $W^2$, $W^3$ and $W^4$ is an oxygen atom or a sulfur atom; and m is 0 or 1, is provided.

29 Claims, No Drawings

REMEDIES OR PREVENTIVES FOR LIVER DISEASES CONTAINING DIAMINOTRIFLUOROMETHYLPYRIDINE DERIVATIVES

TECHNICAL FIELD

The present invention relates to a therapeutic or preventive agent for liver diseases, containing as an active ingredient a diaminotrifluoromethylpyridine derivative or its salt.

BACKGROUND ART

Japanese Patent No. 2762323 and U.S. Pat. No. 5,229,403 disclose that a diaminotrifluoromethylpyridine derivative or its salt has a phospholipase $A_2$ inhibitory action and is useful as an active ingredient of an anti-inflammatory agent or an anti-pancreatitis agent. They also disclose that (1) phospholipase $A_2$ is secreted or activated in platlets or inflammatory cells by stimulations and contributes to the production of a platlet activating factor (PAF) and arachidonic acid metabolites, (2) the arachidonic acid metabolites are closely related to various diseases, for example, inflammatory symptoms such as rheumatic arthritis, arthritis deformans, tendinitis, bursitis, psoriasis and related dermatitis; nasal and bronchial airway troubles such as allergic rhinitis and allergic bronchial asthma; and immediate hypersensitive reactions such as allergic conjunctivitis, (3) on the other hand, phospholipase $A_2$ secreted from pancreas is activated in the intestine and exhibits a digestive action, but once activated in the pancreas, it is believed to be one of the factors causing pancreatitis, and (4) the above diaminotrifluoromethylpyridine derivative inhibits phospholipase $A_2$ and thus is effective for treatment of diseases related to phospholipase $A_2$ such as inflammatory symptoms, nasal and bronchial airway troubles, immediate hypersensitive reactions or pancreatitis, and can be used as an anti-inflammatory agent, an agent for treating bronchial asthma, an anti-allergy agent, an anti-pancreatitis agent, an anti-nephritis agent or an anti-multiple organ failure agent.

Further, U.S. Pat. No. 5,492,908 discloses that such compounds can be used as a therapeutic agent for rheumatoid arthritis, and JP-A-10-298076 discloses that some of these compounds are effective as an anticancer agent having a carcinogenesis inhibitory effect.

As liver diseases, many diseases have been known such as acute hepatitis, fulminant hepatitis, chronic hepatitis, hepatic cirrhosis, fatty liver, alcoholic hepatopathy, drug induced hepatopathy (drug addiction hepatitis), congestive hepatitis, autoimmune hepatitis, primary biliary cirrhosis and hepatic porphyria, and pericholangitis, sclerosing cholangitis, hepatic fibrosis and chronic active hepatitis, which have been reported to occur with a high frequency as complications of inflammatory bowel diseases such as ulcerative colitis and Crohn's disease. Their causes are also various, and acute or chronic hepatopathy based on various causes such as hepatitis virus, drug, alcohol, poisonous substance, autoimmune dysfunction, dysbolism, abnormality of hepatic circulatory system and biliary obstruction, is related by itself or compositely. The treatment of the liver diseases is in principle prevention of progress of hepatic necrocytosis, acceleration of hepatic regeneration, curing of dysbolism, countermeasure of complications and removal of the cause such as virus. Further, it has been clarified that most of liver cancer occurs based on hepatic cirrhosis, and accordingly early treatment with a purpose of preventing the symptoms from being fulminant and progressing to hepatic cirrhosis is considered to be clinically important in treatment of acute hepatitis and chronic hepatitis.

As therapeutic agents of the liver diseases based on this principle, two types of drugs i.e. drugs oriented towards palliative treatment represented by a liver function improving agent (liver protecting agent) and drugs oriented towards liver function improvement and causal treatment, have been used. As examples of the former, nutritional supplementary agents such as a special composition amino acid transfusion and a glucose liquid, glycyrrhizin preparations, germanium preparations (such as propagermanium), Chinese herbal remedy Sho saiko-to, glutathione, cysteine, liver extract agents, polyenephosphatidylcholine, diisopropylamine-dichloroacetate, tiopronin, protoporphyrin, methyl-methionine-sulfonium-chloride, adenosine triphosphate and ursodeoxycholic acid are known. On the other hand, as examples of the latter, adrenocortical hormones such as predonisolone, anti-inflammatory and immunosuppressant agents such as 6-mercaptopurine and D-penicillamine, antiviral agents such as vidarabine (Ara-A) and interferon agents are known. Further, together with the treatment with such drugs, treatment by means of an artificial liver assisting apparatus such as plasma exchange, active carbon hemoperfusion or high permeability hemodialysis, with a purpose of curing dysbolism, may be carried out in some cases. Further, in recent years, new therapeutic agents against the liver diseases have been developed. For example, recombinant human hepatocyte growth factor (JP-A-5-111383), a 1,3-benzoxathiol-2-thione derivative (JP-A-6-239856), a cholestanone derivative (JP-A-7-69898) and a 3-hydroxy-2,3-dihydrobenzofuran derivative (JP-A-11-228563) have been known to be useful as an active ingredient for treatment of the liver diseases. However, although treatment with an existing commercially available drug achieves a certain result on each indication, since causes of the disease, underlying diseases and complications of the liver diseases are various, effectiveness by single administration is limited. Further, there is a fear of adverse reactions and harmful phenomena by drug treatment. For example, with respect to the glycyrrhizin preparation, a case has been reported where adverse reactions along with appearance of pseudo-aldosterone action become problematic. With respect to treatment with a drug having SH groups such as glutathione or cysteine, although detoxication due to the active SH groups is obtained, such a drug may decrease the efficacy of other drug to be used together in some cases. Further, treatment with an adrenocortical hormone may cause infectious diseases or adverse reactions such as thymus or adrenal gland atrophy, and careful administration under hospitalization control is basically required. Further, with respect to the interferon preparation, adverse reactions such as pyrexia and hypoleukocytemia occur with a high frequency, and severe adverse reactions such as pneumonitis (pulmonary fibrosis), autoimmune disease (thyroiditis), neuropsychological dysfunction and cardiomyopathy may occur by its long-term administration. Under these circumstances, development of more effective and safer therapeutic agents for liver diseases has been desired in the clinical field.

DISCLOSURE OF THE INVENTION

The present inventors have conducted extensive studies on pharmacological effects of diaminotrifluoromethylpyridine derivatives or their salts and as a result, found that these compounds are extremely effective as a therapeutic or preventive agent for liver diseases, and the present invention has been accomplished on the basis of this discovery.

The present invention provides a therapeutic agent for liver diseases, containing as an active ingredient a diaminotrifluoromethylpyridine derivative represented by the formula (I) or its salt:

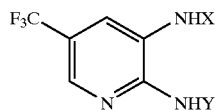
(I)

wherein X is a —CW$^1$R$^1$ group, a —COCOR$^2$ group, a —CW$^1$NHCOR$^2$ group, a —C(=W$^1$)W$^2$R$^3$ group or a —CW$^1$N(R$^4$)R$^5$ group; Y is an alkyl group, a —CW$^3$R$^6$ group, a —COCOR$^7$ group, a —NHCOR$^7$ group, a —C(=W$^3$)W$^4$R$^8$ group, a —(NH)$_m$SO$_2$R$^9$ group, a —(NH)$_m$SO$_2$OR$^{10}$ group or a —(NH)$_m$SO$_2$N(R$^{11}$)R$^{12}$ group; each of R$^1$, R$^6$ and R$^9$ which are independent of one another, is a chain hydrocarbon group which may be substituted, a monocyclic hydrocarbon group which may be substituted, a polycyclic hydrocarbon group which may be substituted, a monocyclic heterocycle group which may be substituted or a polycyclic heterocycle group which may be substituted; each of R$^2$ and R$^7$ which are independent of each other, is an alkyl group which may be substituted, an alkoxy group which may be substituted, a phenyl group which may be substituted or a phenoxy group which may be substituted; each of R$^3$, R$^8$ and R$^{10}$ which are independent of one another, is an alkyl group which may be substituted, an alkenyl group which may be substituted, an alkynyl group which may be substituted, a cycloalkyl group which may be substituted, a phenyl group which may be substituted or a benzyl group which may be substituted; each of R$^4$, R$^5$, R$^{11}$ and R$^{12}$ which are independent of one another, is an alkyl group which may be substituted; each of W$^1$, W$^2$, W$^3$ and W$^4$ which are independent of one another, is an oxygen atom or a sulfur atom; and m is 0 or 1, excluding a case where one of X and Y is a —COCF$_2$X$^1$ group (wherein X$^1$ is a hydrogen atom, a halogen atom, an alkyl group or a haloalkyl group), and the other is a —COCF$_2$X$^2$ group (wherein X$^2$ is a hydrogen atom, a halogen atom, an alkyl group, a haloalkyl group or an alkylcarbonyl group), a —COOX$^3$ group (wherein X$^3$ is an alkyl group which may be substituted or a phenyl group which may be substituted) or a —COX$^4$ group (wherein X$^4$ is an alkyl group, a haloalkyl group, an alkenyl group, an alkynyl group, a phenyl group which may be substituted, a furanyl group or a naphthyl group).

In the formula (I), the above chain hydrocarbon group for each of R$^1$, R$^6$ and R$^9$ may, for example, be an alkyl group, an alkenyl group or an alkynyl group. The above monocyclic hydrocarbon group may, for example, be a cycloalkyl group, a cycloalkenyl group or a phenyl group. The polycyclic hydrocarbon group may be a condensed polycyclic hydrocarbon group such as a naphthyl group, a tetrahydronaphthyl group or an indanyl group, or a bridged polycyclic hydrocarbon group such as an adamantyl group, a noradamantyl group, a norbornanyl group or a norbornanonyl group. The above monocyclic heterocycle group may, for example, be a pyrrolyl group, a furanyl group, a thienyl group, a pyrazolyl group, an imidazolyl group, an oxazolyl group, an isoxazolyl group, a thiazolyl group, an isothiazolyl group, a thiadiazolyl group, a pyrrolinyl group, a pyrrolidinyl group, a dihydrofuranyl group, a tetrahydrofuranyl group, a dihydrothienyl group, a tetrahydrothienyl group, a pyrazolinyl group, a hydantoinyl group, an oxazolinyl group, an isoxazolinyl group, an isoxazolidinyl group, a thiazolinyl group, a thiazolidinyl group, a dioxolanyl group, a dithiolanyl group, a pyridyl group, a pyridazinyl group, a pyrimidinyl group, a pyrazinyl group, a dihydropyridyl group, a tetrahydropyridyl group, a piperidinyl group, a dihydrooxopyridazinyl group, a tetrahydrooxopyridazinyl group, a dihydrooxopyrimidinyl group, a tetrahydrooxopyrimidinyl group, a piperazinyl group, a dihydropyranyl group, a tetrahydropyranyl group, a dioxanyl group, a dihydrodithinyl group, a dithianyl group or a morphorinyl group. The above polycyclic heterocycle group may be a condensed polycyclic heterocycle group such as a thienothienyl group, a dihydrocyclopentathienyl group, an indolyl group, a benzofuranyl group, a benzothienyl group, a benzoxazolyl group, a benzisoxazolyl group, a benzothiazolyl group, a benzimidazolyl group, a tetrahydrobenzothienyl group, a dihydrobenzofuranyl group, a tetrahydrobenzisoxazolyl group, a benzodioxolyl group, a quinolinyl group, an isoquinolinyl group, a benzodioxanyl group or a quinoxalinyl group, or a bridged polycyclic heterocycle group such as a quinuclidinyl group.

The substituent for each of the chain hydrocarbon group which may be substituted for each of R$^1$, R$^6$ and R$^9$ the alkyl group which may be substituted and the alkoxy group which may be substituted for each of R$^2$ and R$^7$, the alkyl group which may be substituted, the alkenyl group which may be substituted and the alkynyl group which may be substituted for each of R$^3$, R$^8$ and R$^{10}$, the alkyl group which may be substituted for each of R$^4$, R$^5$, R$^{11}$ and R$^{12}$ and the alkyl group which may be substituted for X$^3$, may, for example, be a halogen atom, an alkoxy group, a haloalkoxy group, an alkylthio group, a cycloalkyl group, a cycloalkoxy group, a cycloalkenyl group, a cycloalkenyloxy group, an alkoxycarbonyl group, an alkylcarbonyl group, an alkylcarbonyloxy group, an aryl group, an aryloxy group, an arylthio group, an amino group or an amino group substituted with an alkyl group. The number of such substituents or substituents on such substituents may be one or more, and when the number is two or more, such substituents may be the same or different.

Further, the substituent for each of the monocyclic hydrocarbon group which may be substituted, the polycyclic hydrocarbon group which may be substituted, the monocyclic heterocycle group which may be substituted and the polycyclic heterocycle group which may be substituted for each of R$^1$, R$^6$ and R$^9$, the phenyl group which may be substituted and the phenoxy group which may be substituted for each of R$^2$ and R$^7$, the cycloalkyl group which may be substituted, the phenyl group which may be substituted and the benzyl group which may be substituted for each of R$^3$, R$^8$ and R$^{10}$, and the phenyl group which may be substituted for X$^3$, may, for example, be a halogen atom, an alkyl group, a haloalkyl group, an alkoxy group, a haloalkoxy group, an alkylthio group, a cycloalkyl group, a cycloalkoxy group, a cycloalkenyl group, a cycloalkenyloxy group, an alkoxycarbonyl group, an alkylcarbonyl group, an alkylcarbonyloxy group, an aryl group, an aryloxy group, an arylthio group, an amino group, an amino group substituted with an alkyl group, a cyano group or a nitro group. The number of such substituents or substituents on such substituents may be one or more, and when the number is two or more, such substituents may be the same or different.

In the formula (I), the alkyl group and the alkyl moiety contained in each of X and Y may, for example, be C$_{1-18}$ alkyl such as a methyl group, an ethyl group, a propyl group, a butyl group, a pentyl group, a hexyl group, a heptyl group, an octyl group, a decyl group or a nonadecyl group, and they include linear or branched aliphatic structural isomers. The alkenyl group and the alkenyl moiety contained in each of X and Y may be C$_{2-18}$ alkenyl such as a vinyl group, a propenyl group, a butenyl group, a pentenyl group, a hexenyl group, a decenyl group or a nonadecenyl group, and they include linear or branched aliphatic structural isomers. The alkynyl group and the alkynyl moiety contained in each of X and Y may be $C_{2-18}$ alkynyl such as an ethynyl group, a propynyl group, a butynyl group, a pentynyl group, a hexynyl group, a decynyl group or a nonadecynyl group, and they include linear or branched aliphatic structural isomers. The cycloalkyl group and the cycloalkyl moiety contained in each of X and Y may be $C_{3-8}$ cycloalkyl such as a cyclopropyl group, a cyclobutyl group, a cyclopentyl group, a cyclohexyl group or a cyclooctyl group. The cycloalkenyl group and the cycloalkenylmoiety contained in each of X and Y may be $C_{5-8}$ cycloalkenyl such as a cyclopentenyl group, a cyclohexenyl group or a cyclooctenyl group. Further, the halogen atom contained in each of X and Y may be a fluorine atom, a chlorine atom, a bromine atom or an iodine atom. The aryl group and the aryl moiety contained in each of X and Y may, for example, be a phenyl group, a thienyl group, a furanyl group, a pyridyl group, a naphthyl group, a benzothienyl group, a benzofuranyl group or a quinolinyl group.

Now, preferred embodiments of the compounds of the present invention will be described. In the formula (I), it is preferred that X is a —$CW^1R^1$ group or a —$C(=W^1)W^2R^3$ group and Y is a —$SO_2R^9$ group. Each of $R^1$ and $R^6$ is preferably an alkyl group which may be substituted, an alkenyl group which may be substituted, a cycloalkyl group which may be substituted, a cycloalkenyl group which may be substituted, a phenyl group which may be substituted, a tetrahydronaphthyl group which may be substituted, an indanyl group which may be substituted, a furanyl group which may be substituted or a thienyl group which may be substituted. It is more preferably an alkyl group, a haloalkyl group, an alkoxycarbonylalkyl group, an alkenyl group, a haloalkenyl group, an alkenyl group substituted with a thienyl group, a cycloalkyl group, a cycloalkyl group substituted with a halogen atom, a phenyl group, a phenyl group substituted with a halogen atom, a phenyl group substituted with an alkyl group or a haloalkyl group, a phenyl group substituted with an alkoxy group or a haloalkoxy group, a tetrahydronaphthyl group, an indanyl group, a furanyl group or a thienyl group. Each of $R^2$ and $R^7$ is preferably an alkoxy group which may be substituted or a phenyl group which may be substituted. It is more preferably an alkoxy group, a haloalkoxy group, a phenyl group or a phenyl group substituted with a halogen atom. Each of $R^{3,}$ $R^8$ and $R^{10}$ is preferably an alkyl group which may be substituted. It is more preferably an alkyl group or a haloalkyl group. Each of $R^4$, $R^5$, $R^{11}$ and $R^{12}$ is preferably an alkyl group. $R^9$ is preferably an alkyl group which may be substituted, an alkenyl group which may be substituted, a cycloalkyl group which may be substituted, a cycloalkenyl group which may be substituted or a phenyl group which may be substituted. It is more preferably an alkyl group, a haloalkyl group, a phenyl group, a phenyl group substituted with a halogen atom, a phenyl group substituted with an alkyl group or a haloalkyl group or a phenyl group substituted with an alkoxy group or a haloalkoxy group.

Preferred compounds among the compounds of the present invention are compounds of the above formula (I) wherein X is an alkoxycarbonylalkylcarbonyl group, an alkenylcarbonyl group, an alkenylcarbonyl group substituted with a thienyl group, a cycloalkylcarbonyl group, an indanylcarbonyl group, a thiophenecarbonyl group, a tetrahydronaphthylcarbonyl group or a benzoyl group which may be substituted with a halogen atom or a haloalkyl group, and Y is an alkylsulfonyl group. Specific compounds include N-(2-methylsulfonylamino-5-trifluoromethyl-3-pyridyl) acrylamide, N-(2-ethylsulfonylamino-5-trifluoromethyl-3-pyridyl)crotonamide, N-(2-ethylsulfonylamino-5-trifluoromethyl-3-pyridyl)cyclohexanecarboxamide, N-(2-methylsulfonylamino-5-trifluoromethyl-3-pyridyl) cyclohexanecarboxamide, N-(2-methylsulfonylamino-5-trifluoromethyl-3-pyridyl)cyclopentanecarboxamide, N-(2-n-propylsulfonylamino-5-trifluoromethyl-3-pyridyl)-6-(1, 2, 3, 4-tetrahydronaphthalene)carboxamide, N-(2-methylsulfonylamino-5-trifluoromethyl-3-pyridyl)-5-indancarboxamide, N-(2-methylsulfonylamino-5-trifluoromethyl-3-pyridyl)acetoxyacetamide, N-(2-methylsulfonylamino-5-trifluoromethyl-3-pyridyl) crotonamide, N-(2-methylsulfonylamino-5-trifluoromethyl-3-pyridyl)-2-thiophenecarboxamide, N-(2-methylsulfonylamino-5-trifluoromethyl-3-pyridyl)-3-trifluoromethylbenzamide, N-(2-ethylsulfonylamino-5-trifluoromethyl-3-pyridyl)-3-fluorobenzamide, N-(2-methylsulfonylamino-5-trifluoromethyl-3-pyridyl)-6-(1, 2, 3, 4-tetrahydronaphthalene)carboxamide and N-(2-methylsulfonylamino-5-trifluoromethyl-3-pyridyl)-3-(2-thienyl)acrylamide, and their salts.

More preferred compounds may be compounds of the above formula (I) wherein X is a cycloalkylcarbonyl group, an alkenylcarbonyl group or a tetrahydronaphthylcarbonyl group, and Y is an alkylsulfonyl group. Specific compounds include N-(2-ethylsulfonylamino-5-trifluoromethyl-3-pyridyl)cyclohexanecarboxamide, N-(2-methylsulfonylamino-5-trifluoromethyl-3-pyridyl) acrylamide, N-(2-methylsulfonylamino-5-trifluoromethyl-3-pyridyl)cyclohexanecarboxamide, N-(2-methylsulfonylamino-5-trifluoromethyl-3-pyridy) cyclopentanecarboxamide and N-(2-n-propylsulfonylamino-5-trifluoromethyl-3-pyridyl)-6-(1, 2, 3, 4-tetrahydronaphthalene)carboxamide, and their salts.

The compounds represented by the formula (I) may form a salt when Y is a —$SO_2R^9$ group (wherein $R^9$ is as defined above). Such a salt may be any pharmaceutically acceptable salt, for example, an alkali metal salt such as a potassium salt or a sodium salt, an alkaline earth metal salt such as a calcium salt, or an organic amine salt such as a triethanolamine salt or a tris(hydroxymethyl)aminomethane salt. Such a salt may have crystal water.

The compounds represented by the formula (I) can be prepared, for example, by a process as disclosed in Japanese Patent No. 2762323. Further, these compounds have geometrical isomers depending upon the type of their substituents, and the present invention includes isomers (cis-forms and trans-forms) and isomer mixtures.

The compounds of the present invention represented by the above formula (I) are useful as an active ingredient for a therapeutic or preventive agent for liver diseases. They are useful as an active ingredient for a therapeutic or preventive agent for, among various liver diseases, liver diseases (hepatopathy, liver insufficiency) such as acute hepatitis, fulminant hepatitis, chronic hepatitis, hepatic cirrhosis, fatty liver, alcoholic hepatopathy, drug induced hepatopathy (drug addiction hepatitis), congestive hepatitis, autoimmune hepatitis, primary biliary cirrhosis and hepatic porphyria, and pericholangitis, sclerosing cholangitis, hepatic fibrosis and chronic active hepatitis, which have been reported to occur with a high frequency as complications of inflammatory bowel diseases such as ulcerative colitis and Crohn's disease. They are particularly useful as an active ingredient for a therapeutic or preventive agent for liver diseases (hepatopathy, liver insufficiency) such as acute hepatitis, fulminant hepatitis, chronic hepatitis, hepatic cirrhosis, fatty liver, alcoholic hepatopathy, drug induced hepatopathy (drug addiction hepatitis), congestive hepatitis, autoimmune hepatitis, primary biliary cirrhosis and hepatic porphyria. The compounds of the present invention are particularly useful as a therapeutic or preventive agent for hepatopathy (drug induced hepatopathy, drug addiction hepatitis) due to a drug such as acetaminophen, and hepatopathy due to ischemia repurfusion. Further, they are expected to be more effective by combination with another drug such as Chinese herbal remedy.

To administer the compound of the present invention as an active ingredient for a therapeutic agent for liver diseases, it is formulated alone or together with a pharmaceutically acceptable carrier into a drug composition suitable for peroral or parenteral administration, such as a tablet, a powder, a capsule, a granule, an injection drug, an ointment, an inhalant, an enema or a suppository, and it is administered in the form of such a drug formulation.

As a drug formulation suitable for peroral administration, a solid composition such as a tablet, a capsule, a powder, a granule or a troach; or a liquid composition such as a syrup suspension, may, for example, be mentioned. The solid composition such as a tablet, a capsule, a powder, a granule or a troach may contain a binder such as fine crystalline cellulose, gum arabic, tragacanth gum, gelatine or polyvinyl pyrrolidone; a excipient such as starch, lactose or carboxymethyl cellulose; a disintegrator such as arginic acid, corn starch or carboxymethyl cellulose; a lubricant such as magnesium stearate, light silicic anhydride or colloidal silicon dioxide; a sweetener such as sucrose; or a flavoring agent such as peppermint or methyl salicylate. The liquid composition such as a syrup or a suspension may contain sorbitol, gelatine, methyl cellulose, carboxymethyl cellulose, a vegetable oil such as a peanut oil, an emulsifier such as lecithin as well as a sweetener, a preservative, a colorant or a flavoring agent, as the case requires. Such a composition may be provided in the form of a dried formulation. These formulations preferably contain from 1 to 95 wt % of the active ingredient compound.

A drug formulation suitable for parenteral administration may, for example, be an injection drug. The injection drug may be prepared by dissolving the compound in the form of a salt in usual water for injection, or may be formulated into a formulation suitable for injection such as a suspension or an emulsion (in a mixture with a medically acceptable oil or liquid). In such a case, it may contain benzyl alcohol as an antibacterial agent, ascorbic acid as an antioxidant, a medically acceptable buffer solution or a reagent for adjusting the osmotic pressure. Such an injection drug preferably contains from 0.1 to 8 wt % of the active ingredient compound.

A drug formulation suitable for topical or per rectal administration may, for example, be an inhalant, an ointment, an enema or a suppository. The inhalant may be formulated by dissolving the compound of the present invention alone or together with a medically acceptable inert carrier in an aerosol or nebulizer solution, or may be administered to the respiratory airway in the form of fine powder for inhalation. In the case of fine powder for inhalation, the particle size is usually not more than 50µ, preferably not more than 10µ. Such an inhalant may be used, if necessary, in combination with other antiasthematic agent or bronchodilator.

An ointment may be prepared by a conventional method by an addition of e.g. a commonly employed base. The ointment preferably contains from 0.1 to 30 wt % of the active ingredient compound.

A suppository may contain a carrier for formulation which is well known in this field, such as polyethylene glycol, lanolin, cacao butter or fatty acid triglyceride. The suppository preferably contains from 1 to 95 wt % of the active ingredient compound.

The above drug compositions suitable for peroral, parenteral, topical or per rectal administration, may be formulated by known methods so that after administration to a patient, the active ingredient will be rapidly discharged, gradually discharged or belatedly discharged.

Needless to say, the dose of the compound of the present invention varies depending upon the type of the compound, the administration method, the condition of the patient or the animal to be treated, and the optimum dose and the number of administration under a specific condition must be determined by the judgment of a competent doctor. Usually, however, a daily dose to an adult is from about 0.1 mg to about 10 g, preferably from about 1 mg to about 1 g. In the case of the above inhalation method, the dose of the compound of the present invention is preferably from about 0.01 mg to about 1 g per administration.

Now, specific Formulation Examples of the therapeutic agent for liver diseases of the present invention will be given. However, the formulation of the present invention is not limited thereto.

FORMULATION EXAMPLE 1

Tablet

| | |
|---|---|
| (1) Active ingredient | 20 mg |
| (2) Lactose | 150 mg |
| (3) Starch | 30 mg |
| (4) Magnesium stearate | 6 mg |

The above composition is tabletted so that the components (1) to (4) constitute one tablet.

FORMULATION EXAMPLE 2

Powder, Subtilized Granule or Granule

| | |
|---|---|
| (1) Active ingredient | 20 mg |
| (2) Sugar ester (DK ester F-160, tradename, manufactured by DAI-ICHI KOGYO SEIYAKU CO., LTD.) | 180 mg |
| (3) Surfactant (DEKA-GREEN 1-L, tradename, manufactured by Nikko Chemicals Co., Ltd.) | 15 mg |
| (4) Light silicic anhydride | 25 mg |

The above components (1) to (4) are mixed and formed into a powder, or subtilized granule or granule by granulation. Such a powder, subtilized granule or granule may be sealed in a capsule to obtain a capsule drug.

FORMULATION EXAMPLE 3

Hard Gelatine Capsule Drug

| | |
|---|---|
| (1) Active ingredient | 25 mg |
| (2) Starch | 200 mg |
| (3) Magnesium stearate | 10 mg |

The above components (1) to (3) are packed in one hard gelatine capsule to obtain a hard gelatine capsule drug.

FORMULATION EXAMPLE 4

Injection Drug

| | |
|---|---|
| (1) Active ingredient | 1 mg |
| (2) Glucose | 10 mg |
| (3) Tris (hydroxymethyl) aminomethane | 2.16 mg |

A tris buffer containing the components (1) to (3) is freeze-dried to prepare an injection drug.

FORMULATION EXAMPLE 5

Ointment for External Skin Application

| | |
|---|---|
| (1) Active ingredient | 0.5 g |
| (2) White vaseline | 25 g |
| (3) Stearyl alcohol | 22 g |
| (4) Propylene glycol | 12 g |
| (5) Sodium lauryl sulfate | 1.5 g |
| (6) Ethyl parahydroxybenzoate | 0.025 g |
| (7) Propyl parahydroxybenzoate | 0.015 g |
| (8) Purified water | 100 g |

The components (1) to (8) are formulated into an ointment for external skin application by a usual method for preparation of an ointment.

FORMULATION EXAMPLE 6

Enema Formulation

| | |
|---|---|
| (1) Active ingredient | 50 mg |
| (2) Macrogol 400 | 2 g |
| (3) Dipotassium phosphate | 141 mg |
| (4) Potassium dihydrogenphosphate | 44 mg |
| (5) Methyl parahydroxybenzoate | 20 mg |
| (6) Purified water | 50 g |

The active ingredient and methyl parahydroxybenzoate are added to Macrogol 400, followed by stirring to obtain a mixture, to which one obtained by adding dipotassium phosphate and potassium dihydrogenphosphate to the purified water is gradually added to prepare an enema formulation.

FORMULATION EXAMPLE 7

Suppository

| | |
|---|---|
| (1) Active ingredient | 50 mg |
| (2) Higher fatty acid glyceride | 1,650 mg |

The component (1) is dispersed or dissolved in (2), and packed and sealed in a plastic container having a size appropriate as a suppository, followed by cooling for solidification to prepare a suppository.

FORMULATION EXAMPLE 8

Rectum Remaining Suppository, Controlled Release Suppository

| | |
|---|---|
| (1) Active ingredient | 1 g |
| (2) Witepsol W35 | 19 g |

The component (1) is admixed with preliminarily heated and dissolved (2), and the admixture is packed and sealed in a plastic container having a size appropriate as a suppository, followed by cooling for solidification to prepare a suppository.

EXAMPLES

Test Example 1

Therapeutic Effect on Mouse Acetaminophen Hepatopathy Model

The therapeutic effect of N-(2-ethylsulfonylamino-5-trifluoromethyl-3-pyridyl)cyclohexanecarboxamide sodium salt hydrate (hereinafter referred to as compound 1) on acetaminophen (APAP) induced mouse hepatopathy model was examined.

To Crj: CD-1(ICR) male mice (6 weeks old) (Charles River Japan Inc.), APAP (Lot. No. 107H0332, manufactured by Sigma) dissolved with physiological saline (Lot No. 80909D manufactured by Fuso Pharmaceutical Industries, Ltd.) was intraperitoneally administered in an amount of the active ingredient of 300 mg/kg to induce hepatopathy. 3 Hours after the administration of APAP, the compound 1 dissolved in physiological saline was singly administered subcutaneously on the back in an amount of the active ingredient of 10 mg/kg. To non-treated group mice, physiological saline was similarly administered. 6 Hours after the administration of APAP, the blood was collected, and glutamic-oxaloacetic transaminase (GOT) and glutamic-pyruvic transaminase (GPT) values in the blood serum were measured. The results are shown in Table 1.

In the present test, mice were kept on a fast from 20 hours before the administration of APAP until the completion of the test.

TABLE 1

| | Biochemical examination values (mean ± standard deviation) N = 5 | |
|---|---|---|
| Group | GOT (IU/L) | GPT (IU/L) |
| Non-treated group (physiological saline) | 4183 ± 2940 | 5649 ± 4409 |
| Treated group (compound 1) | 530 ± 212 | 807 ± 603 |

In the non-treated group, the biochemical examination values to be indices of hepatopathy increased due to acetaminophen, whereas in the group treated with the compound 1, increases in the examination values were suppressed, and it was confirmed that the hepatopathy was alleviated as compared with the acetaminophen induced mouse hepatopathy model.

Test Example 2

Therapeutic Effect on Rat Liver Ischemia Reperfusion Hepatopathy Model

The therapeutic effect of the compound 1 on rat hepatopathy model induced by partially subjecting the liver to ischemia reperfusion was examined.

(1) The compound 1 was used as a drug formulation. The formulation composition (content per one vial) was as follows.

| | |
|---|---|
| (a) Compound 1 (as anhydride) | 100 mg |
| (b) D-mannitol (manufactured by KYOWA HAKKO KOGYO CO., LTD.) | 100 mg |
| (c) Tris (hydroxymethyl) aminomethane (manufactured by JUNSEI CHEMICAL) | 21.6 mg |
| (d) Hydrochloric acid (manufactured by SANKYO KAGAKU) | optimum amount |
| (e) Sodium hydroxide (manufactured by Nippon Rika) | optimum amount |
| (f) Distilled water | 10 ml |
| pH 8.7 ± 0.5 | |

(2) Crj:SD (IGS) male rats (7 weeks old) (Charles River Japan, Inc.) were anesthetized with ether, and while maintaining them anesthetized with gas-oxygen fluothane, the above drug formulation of the compound 1 diluted with 5% glucose (Lot. 9I78N, manufactured by Otsuka Pharmaceutical Factory, Inc.) so that the dose would be 10 mg/kg/hr as calculated as anhydride of the compound 1, was subcutaneously administered singly. Then, an osmotic pump (alzet osmotic pump 2001D, ALZA CORPORATION, U.S.A.) in which the above drug formulation of the compound 1 diluted with 5% glucose (Lot. 9I78N, manufactured by Otsuka Pharmaceutical Factory, Inc.) so that the dose would be 0.3 mg/kg/hr as calculated as anhydride of the compound 1 was put, was embedded in the dorsal cervical subcutaneous. To non-treated group rats, 5% glucose alone was administered similarly. Then, the ventral midline was incised, and arbor of the portal vein of the quadratic lobe, left medial and lateral lobes of the liver, were completely blocked by means of a clamp (about 70% of the entire liver was under ischemia). The abdomen was closed, the rats were awaked, and after 90 minutes, the abdomen was opened up again under the above-described anesthesia, the clamp was removed and the rats were subjected to reperfusion. To pseudo-induced group rats, operation except for the ischemia reperfusion treatment was carried out. The abdomen was closed and the rats were awaked, and 6 hours after the reperfusion, aspartate aminotransferase (AST) and alanine aminotransferase (ALT), lactate dehydrogenase (LDH) and total bilirubin values in the blood serum were measured. The results are shown in Table 2.

TABLE 2

Biochemical examination values (mean ± standard deviation) N = 10

| Group | AST (GOT) (IU/L) | ALT (GPT) (IU/L) | LDH (IU/L) | Total bilirubin (mg/dL) |
|---|---|---|---|---|
| Pseudo-induced group | 128 ± 23 | 24 ± 5 | 1370 ± 291 | 0.070 ± 0.024 |
| Non-treated group (5% glucose) | 12304 ± 5096 | 6971 ± 3194 | 45826 ± 25233 | 0.447 ± 0.302 |
| Treated group (compound 1) | 8669 ± 5854 | 5436 ± 4952 | 29601 ± 30505 | 0.299 ± 0.192 |

In the non-treated group, the biochemical examination values as indices of the hepatopathy increased by ischemia reperfusion of the liver as compared with the pseudo-induced group, whereas in the group treated with the compound 1, increases in the examination values were suppressed, and it was confirmed that the hepatopathy in the rat ischemia reperfusion hepatopathy model was alleviated.

What is claimed is:
1. A method for preventing or treating a liver or hepatic disease, comprising administering to a subject in need thereof an effective amount of a diaminotrifluoromethylpyridine compound or its salt, wherein said compound is represented by formula (I):

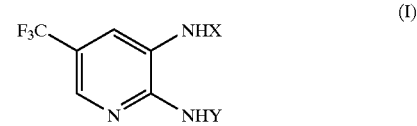

(I)

wherein:
X is a —CW$^1$R$^1$ group, a —COCOR$^2$ group, a —CW$^1$NHCOR$^2$ group, a —C(=W$^1$)W$^2$R$^3$ group or a —CW$^1$N(R$^4$)R$^5$ group;
Y is an alkyl group, a —CW$^3$R$^6$ group, a —COCOR$^7$ group, a —NHCOR$^7$ group, a —C(=W$^3$)W$^4$R$^8$ group, a —(NH)$_m$SO$_2$R$^9$ group, a —(NH)$_m$SO$_2$OR$^{10}$ group or a —(NH)$_m$SO$_2$N(R$^{11}$)R$^{12}$ group;
wherein each of R$^1$, R$^6$ and R$^9$, which are independent of one another, is a chain hydrocarbon group which may be substituted, a monocyclic hydrocarbon group which may be substituted, a polycyclic hydrocarbon group which may be substituted, a monocyclic heterocycle group which may be substituted or a polycyclic heterocycle group which may be substituted;
wherein each of R$^2$ and R$^7$, which are independent of each other, is an alkyl group which may be substituted, an alkoxy group which may be substituted, a phenyl group which may be substituted or a phenoxy group which may be substituted;
wherein each of R$^3$, R$^8$ and R$^{10}$, which are independent of one another, is an alkyl group which may be substituted, an alkenyl group which may be substituted, an alkynyl group which may be substituted, a cycloalkyl group which may be substituted, a phenyl group which may be substituted or a benzyl group which may be substituted;
wherein each of R$^4$, R$^5$, R$^{11}$ and R$^{12}$, which are independent of one another, is an alkyl group which may be substituted;
wherein each of W$^1$, W$^2$, W$^3$ and W$^4$ which are independent of one another, is an oxygen atom or a sulfur atom; and
wherein m is 0 or 1;
with the proviso that said compound of formula (I) is not a compound where one of X and Y is a —COCF$_2$X$^1$ group (wherein X$^1$ is a hydrogen atom, a halogen atom, an alkyl group or a haloalkyl group), and the other is a —COCF$^2$X$^2$ group (wherein X$^2$ is a hydrogen atom, a halogen atom, an alkyl group, a haloalkyl group or an alkylcarbonyl group), a —COOX$^3$ group (wherein X$^3$ is an alkyl group which may be substituted or a phenyl group which may be substituted) or a —COX$^4$ group (wherein X$^4$ is an alkyl group, a haloalkyl group, an alkenyl group, an alkynyl group, a phenyl group which may be substituted, a furanyl group or a naphthyl group).
2. The method of claim 1, wherein
X is a —CW$^1$R$^1$ group or a —C(=W$^1$)W$^2$R$^3$ group and Y is a —SO$_2$R$^9$ group.
3. The method of claim 1, wherein
X is a —CW$^1$R$^1$ group or a —C(=W$^1$)W$^2$R$^3$ group,
R$^1$ is an alkyl group which may be substituted, an alkenyl group which may be substituted, a cycloalkyl group which may be substituted, a cycloalkenyl group which may be substituted, a phenyl group which may be substituted, a tetrahydronaphthyl group which may be substituted, an indanyl group which may be substituted, a furanyl group which may be substituted or a thienyl group which may be substituted, $R^3$ is an alkyl group which may be substituted, Y is a —$SO_2R^9$ group, and $R^9$ is an alkyl group which may be substituted, an alkenyl group which may be substituted, a cycloalkyl group which may be substituted, a cycloalkenyl group which may be substituted or a phenyl group which may be substituted.

4. The method of claim 1, wherein

X is a —$CW^1R^1$ group or a —$C(=W^1)W^2R^3$ group, $R^1$ is an alkyl group, a haloalkyl group, an alkoxycarbonyl alkyl group, an alkenyl group, a haloalkenyl group, an alkenyl group substituted with a thienyl group, a cycloalkyl group, a cycloalkyl group substituted with a halogen atom, a phenyl group, a phenyl group substituted with a halogen atom, a phenyl group substituted with an alkyl group or a haloalkyl group, a phenyl group substituted with an alkoxy group or a haloalkoxy group, a tetrahydronaphthyl group, an indanyl group, a furanyl group or a thienyl group, $R^3$ is an alkyl group or a haloalkyl group, Y is a —$SO_2R^9$ group, and $R^9$ is an alkyl group, a haloalkyl group, a phenyl group, a phenyl group substituted with a halogen atom, a phenyl group substituted with an alkyl group or a haloalkyl group, or a phenyl group substituted with an alkoxy group or a haloalkoxy group.

5. The method of claim 1, wherein

X is an alkoxycarbonyl alkylcarbonyl group, an alkenylcarbonyl group, an alkenylcarbonyl group substituted with a thienyl group, a cycloalkylcarbonyl group, an indanylcarbonyl group, a thiophenecarbonyl group, a tetrahydronaphthylcarbonyl group or a benzoyl group which may be substituted with a halogen atom or a haloalkyl group, and Y is an alkylsulfonyl group.

6. The method of claim 1, wherein

X is a cycloalkylcarbonyl group, an alkenylcarbonyl group or a tetrahydronaphthylcarbonyl group, and Y is an alkylsulfonyl group.

7. The method of claim 1, wherein the diaminotrifluoromethylpyridine compound is:
  N-(2-ethylsulfonylamino-5-trifluoromethyl-3-pyridyl) cyclohexanecarboxamide,
  N-(2-methylsulfonylamino-5-trifluoromethyl-3-pyridyl) cyclohexanecarboxamide,
  N-(2-methysulfonylamino-5-trifluoromethyl-3-pyridyl) cyclopentanecarboxamide,
  N-(2-methylsulfonylamino-5-trifluoromethyl-3-pyridyl) acrylamide or
  N-(2-n-propylsulfonylamino-5-trifluoromethyl-3-pyridyl)-6-(1, 2, 3, 4-tetrahydronaphthalene) carboxamide.

8. The method of claim 1, wherein the diaminotrifluoromethylpyridine compound is N-(2-ethylsulfonylamino-5-trifluoromethyl-3-pyridyl)cyclohexane carboxamide.

9. The method of claim 1 that is a method for preventing a liver or hepatic disease.

10. The method of claim 1 that is a method for treating a liver or hepatic disease.

11. The method of claim 1 that comprises treating a disease selected from the group consisting of acute hepatitis, fulminant hepatitis, chronic hepatitis, hepatic cirrhosis, fatty liver, alcoholic hepatopathy, drug induced hepatopathy, drug addiction hepatitis, congestive hepatitis, autoimmune hepatitis, primary biliary cirrhosis and hepatic porphyria, and pericholangitis, sclerosing cholangitis, hepatic fibrosis and chronic active hepatitis.

12. The method of claim 1 comprising treating a subject with drug induced hepatopathy.

13. The method of claim 1 comprising treating a subject with acute hepatitis.

14. The method of claim 1 comprising treating a subject with alcoholic hepatitis.

15. The method of claim 1 comprising treating a subject with autoimmune hepatitis.

16. The method of claim 1 comprising treating a subject with hepatopathy associated with ischemia reperfusion.

17. The method of claim 1, further comprising administering at least one other drug, therapeutic agent or herbal remedy.

18. The method of claim 1 comprising administering an alkaline metal salt, an alkaline earth metal salt or an organic amine salt of said compound.

19. The method of claim 1 comprising administering said compound perorally.

20. The method of claim 19, wherein said compound is formulated in a manner to be rapidly discharged, be gradually discharged, or be belatedly discharged once administered to a subject.

21. The method of claim 1 comprising administering said compound in the form of a tablet, capsule, powder, granule, troche, liquid, suspension, emulsion, ointment, suppository, enema, or syrup.

22. The method of claim 1 comprising administering said compound parenterally.

23. The method of claim 1 comprising administering said compound topically or by rectal administration.

24. The method of claim 1 comprising administering said compound via the respiratory airway or by inhalation.

25. The method of claim 1 comprising administering a daily dose ranging from 0.1 mg to about 10 g of said diaminotrifluoromethylpyridine compound or its salt.

26. The method of claim 1 comprising administering a daily dose ranging from 1 mg to about 1 g of said diaminotrifluoromethylpyridine compound or its salt.

27. A method for decreasing at least one value in an index of hepatopathy comprising administering the diaminotrifluoromethylpyridine compound described by claim 1 or its salt.

28. A method for suppressing the level of glutamic-oxaloacetic transaminase (GOT) or glutamic-pyruvic transaminase (GPT) in the blood serum of a subject with liver disease or hepatopathy comprising administering to said subject the diaminotrifluoromethylpyridine compound described by claim 1 or its salt.

29. A method for suppressing the level of aspartate aminotransferase (AST), alanine aminotransferase (ALT), lactate dehydrogenase (LDH) and/or total bilirubin in the blood serum of a subject with liver disease or hepatopathy comprising administering to said subject the diaminotrifluoromethylpyridine compound described by claim 1 or its salt.

* * * * *

UNITED STATES PATENT AND TRADEMARK OFFICE
CERTIFICATE OF CORRECTION

PATENT NO.    : 6,664,279 B2
DATED         : December 16, 2003
INVENTOR(S)   : Shuichi et al.

It is certified that error appears in the above-identified patent and that said Letters Patent is hereby corrected as shown below:

Column 14,
Line 51, "luoromethylpyridine compound described by claim 1 or its" should read
-- luoromethylpyridine compound described by formula (I):

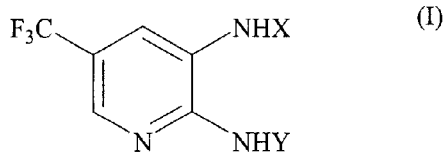

wherein:
X is a $-CW^1 R^1$ group, a $-COCOR^2$ group, a $-CW^1 NHCOR^2$ group, a
   $-C(=W^1)W^2R^3$ group or a $-CW^1N(R^4)R^5$ group;
Y is an alkyl group, a $-CW^3R^6$ group, a $-COCOR^7$ group, a $-NHCOR^7$ group, a
   $-C(=W^3)W^4R^8$ group, a $-(NH)_mSO_2R^9$ group, a $-(NH)_mSO_2OR^{10}$ group or a
   $-(NH)_mSO_2N(R^{11})R^{12}$ group;
wherein each of $R^1$, $R^6$ and $R^9$, which are independent of one another, is a
   chain hydrocarbon group which may be substituted, a monocyclic
   hydrocarbon group which may be substituted, a polycyclic hydrocarbon
   group which may be substituted, a monocyclic heterocycle group which
   may be substituted or a polycyclic heterocycle group which may be
   substituted;
wherein each of $R^2$ and $R^7$, which are independent of each other, is an alkyl
   group which may be substituted, an alkoxy group which may be substituted,
   a phenyl group which may be substituted or a phenoxy group which may be
   substituted;
wherein each of $R^3$, $R^8$ and $R^{10}$, which are independent of one another, is an
   alkyl group which may be substituted, an alkenyl group which may be
   substituted, an alkynyl group which may be substituted, a cycloalkyl group
   which may be substituted, a phenyl group which may be substituted or a
   benzyl group which may be substituted;
wherein each of $R^4$, $R^5$, $R^{11}$ and $R^{12}$, which are independent of one another, is
   an alkyl group which may be substituted;
wherein each of $W^1$, $W^2$, $W^3$ and $W^4$ which are independent of one another, is
   an oxygen atom or a sulfur atom; and
wherein m is 0 or 1;
with the proviso that said compound of formula (I) is not a compound where
   one of X and Y is a $-COCF^2 X^1$ group (wherein $X^1$ is a hydrogen atom, a
   halogen atom, an alkyl group or a haloalkyl group), and the other is a -
   $COCF^2 X^2$ group (wherein $X^2$ is a hydrogen atom, a halogen atom, an alkyl
   group, a haloalkyl group or an alkylcarbonyl group), a $--COOX^3$ group
   (wherein $X^3$ is an alkyl group which may be substituted or a phenyl group
   which may be substituted) or a $-COX^4$ group (wherein $X^4$ is an alkyl group, a
   haloalkyl group, an alkenyl group, an alkynyl group, a phenyl group which
   may be substituted, a furanyl group or a naphthyl group), or its

UNITED STATES PATENT AND TRADEMARK OFFICE
CERTIFICATE OF CORRECTION

PATENT NO. : 6,664,279 B2
DATED : December 16, 2003
INVENTOR(S) : Shuichi et al.

It is certified that error appears in the above-identified patent and that said Letters Patent is hereby corrected as shown below:

Column 14, cont'd,
Line 58, "described by claim 1 or its salt." should read -- described by formula (I):

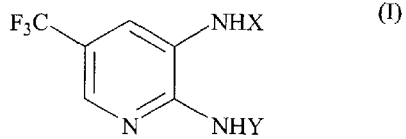

wherein:
X is a $-CW^1R^1$ group, a $-COCOR^2$ group, a $-CW^1NHCOR^2$ group, a $-C(=W^1)W^2R^3$ group or a $-CW^1N(R^4)R^5$ group;
Y is an alkyl group, a $-CW^3R^6$ group, a $-COCOR^7$ group, a $-NHCOR^7$ group, a $-C(=W^3)W^4R^8$ group, a $-(NH)_mSO_2R^9$ group, a $-(NH)_mSO_2OR^{10}$ group or a $-(NH)_mSO_2N(R^{11})R^{12}$ group;
wherein each of $R^1$, $R^6$ and $R^9$, which are independent of one another, is a chain hydrocarbon group which may be substituted, a monocyclic hydrocarbon group which may be substituted, a polycyclic hydrocarbon group which may be substituted, a monocyclic heterocycle group which may be substituted or a polycyclic heterocycle group which may be substituted;
wherein each of $R^2$ and $R^7$, which are independent of each other, is an alkyl group which may be substituted, an alkoxy group which may be substituted, a phenyl group which may be substituted or a phenoxy group which may be substituted;

wherein each of $R^3$, $R^8$ and $R^{10}$, which are independent of one another, is an alkyl group which may be substituted, an alkenyl group which may be substituted, an alkynyl group which may be substituted, a cycloalkyl group which may be substituted, a phenyl group which may be substituted or a benzyl group which may be substituted;
wherein each of $R^4$, $R^5$, $R^{11}$ and $R^{12}$, which are independent of one another, is an alkyl group which may be substituted;
wherein each of $W^1$, $W^2$, $W^3$ and $W^4$ which are independent of one another, is an oxygen atom or a sulfur atom; and
wherein m is 0 or 1;
with the proviso that said compound of formula (I) is not a compound where one of X and Y is a $-COCF^2X^1$ group (wherein $X^1$ is a hydrogen atom, a halogen atom, an alkyl group or a haloalkyl group), and the other is a $-COCF^2X^2$ group (wherein $X^2$ is a hydrogen atom, a halogen atom, an alkyl group, a haloalkyl group or an alkylcarbonyl group), a $-COOX^3$ group (wherein $X^3$ is an alkyl group which may be substituted or a phenyl group which may be substituted) or a $-COX^4$ group (wherein $X^4$ is an alkyl group, a haloalkyl group, an alkenyl group, an alkynyl group, a phenyl group which may be substituted, a furanyl group or a naphthyl group), or its salt.

UNITED STATES PATENT AND TRADEMARK OFFICE
CERTIFICATE OF CORRECTION

PATENT NO. : 6,664,279 B2
DATED : December 16, 2003
INVENTOR(S) : Shuichi et al.

It is certified that error appears in the above-identified patent and that said Letters Patent is hereby corrected as shown below:

Column 14, cont'd,
Line 64, "compound described by claim 1 or its salt." should read -- compound described by formula (I):

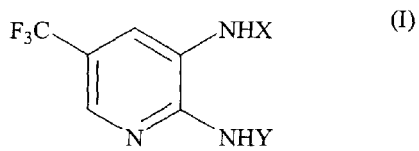

wherein:
X is a $-CW^1 R^1$ group, a $-COCOR^2$ group, a $-CW^1 NHCOR^2$ group, a
 $-C(=W^1)W^2R^3$ group or a $-CW^1N(R^4)R^5$ group;
Y is an alkyl group, a $-CW^3R^6$ group, a $-COCOR^7$ group, a $-NHCOR^7$ group, a
 $-C(=W^3)W^4R^8$ group, a $-(NH)_mSO_2R^9$ group, a $-(NH)_mSO_2OR^{10}$ group or a
 $-(NH)_mSO_2N(R^{11})R^{12}$ group;
wherein each of $R^1$, $R^6$ and $R^9$, which are independent of one another, is a chain
 hydrocarbon group which may be substituted, a monocyclic hydrocarbon
 group which may be substituted, a polycyclic hydrocarbon group which may
 be substituted, a monocyclic heterocycle group which may be substituted or a
 polycyclic heterocycle group which may be substituted;
wherein each of $R^2$ and $R^7$, which are independent of each other, is an alkyl
 group which may be substituted, an alkoxy group which may be substituted, a
 phenyl group which may be substituted or a phenoxy group which may be
 substituted;
wherein each of $R^3$, $R^8$ and $R^{10}$, which are independent of one another, is an
 alkyl group which may be substituted, an alkenyl group which may be
 substituted, an alkynyl group which may be substituted, a cycloalkyl group
 which may be substituted, a phenyl group which may be substituted or a
 benzyl group which may be substituted;
wherein each of $R^4$, $R^5$, $R^{11}$ and $R^{12}$, which are independent of one another,
 is an alkyl group which may be substituted;
wherein each of $W^1$, $W^2$, $W^3$ and $W^4$ which are independent of one another,
 is an oxygen atom or a sulfur atom; and
wherein m is 0 or 1;

UNITED STATES PATENT AND TRADEMARK OFFICE
CERTIFICATE OF CORRECTION

PATENT NO. : 6,664,279 B2
DATED : December 16, 2003
INVENTOR(S) : Shuichi et al.

It is certified that error appears in the above-identified patent and that said Letters Patent is hereby corrected as shown below:

Column 14, cont'd, with the proviso that said compound of formula (I) is not a compound where one of X and Y is a -COCF$_2$ X$^1$ group (wherein X$^1$ is a hydrogen atom, a halogen atom, an alkyl group or a haloalkyl group), and the other is a -COCF$^2$ X$^2$ group (wherein X$^2$ is a hydrogen atom, a halogen atom, an alkyl group, a haloalkyl group or an alkylcarbonyl group), a -COOX$^3$ group (wherein X$^3$ is an alkyl group which may be substituted or a phenyl group which may be substituted) or a -COX$^4$ group (wherein X$^4$ is an alkyl group, a haloalkyl group, an alkenyl group, an alkynyl group, a phenyl group which may be substituted, a furanyl group or a naphthyl group), or its salt.--

Signed and Sealed this

Sixth Day of July, 2004

JON W. DUDAS
*Acting Director of the United States Patent and Trademark Office*